United States Patent [19]
Carroll

[11] 4,251,483
[45] Feb. 17, 1981

[54] MULTIPLE INDEPENDENT PATH BUBBLE TONOMETER

[76] Inventor: Cliff R. Carroll, P.O. Box 767, Glendale, Calif. 91209

[21] Appl. No.: 82,795

[22] Filed: Oct. 9, 1979

[51] Int. Cl.³ .................... G01N 33/50; G01N 33/96; G01N 1/10
[52] U.S. Cl. ....................................... 422/68; 23/928; 261/124; 261/DIG. 28; 422/50; 422/99
[58] Field of Search ................. 23/230 B; 422/50, 68, 422/101, 102, 99; 55/68; 261/112, 122, 82, 124, DIG. 28, 126; 73/421 R, 425.4 R

[56] References Cited
U.S. PATENT DOCUMENTS

| | | | |
|---|---|---|---|
| 3,127,254 | 3/1964 | Astrup et al. | 261/112 X |
| 3,973,915 | 8/1976 | Raffaele | 23/230 B |

OTHER PUBLICATIONS
Noonan et al., Clin. Chem., vol. 20, No. 6, 1974, pp. 660–665.
Adams et al., "Determination of the Blood/Gas Factor of the Oxygen Electrode Using a New Tonometer", British J. of Anaesthesia, C1967, pp. 107–113.

*Primary Examiner*—Ronald Serwin
*Attorney, Agent, or Firm*—Wagner & Bachand

[57] ABSTRACT

Multiple, independent path bubble tonometer apparatus for preparing a plurality of predetermined like or different gas/blood samples under identical though dynamic conditions. The tonometer comprises in a controlled environment common locus, multiple tonometer paths each of which is defined by a gas/blood equilibration chamber, means to add a blood sample to the chamber, means to diffuse a gas into the blood sample to an equilibrium condition therein, the gas diffusion means including a porous diffuser body communicating the sample with a pressurized gas supply, and side arm means to selectively withdraw an aliquot portion of the equilibrium condition sample; and an enclosure defining the controlled environment locus identically about each and every tonometer path for instantly cross-referenceable multiple sample preparations.

11 Claims, 5 Drawing Figures

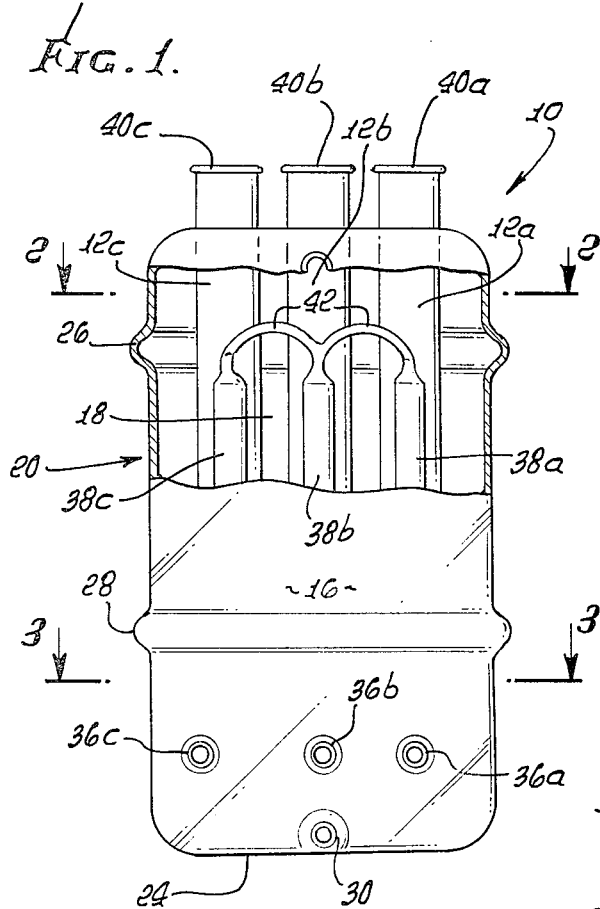
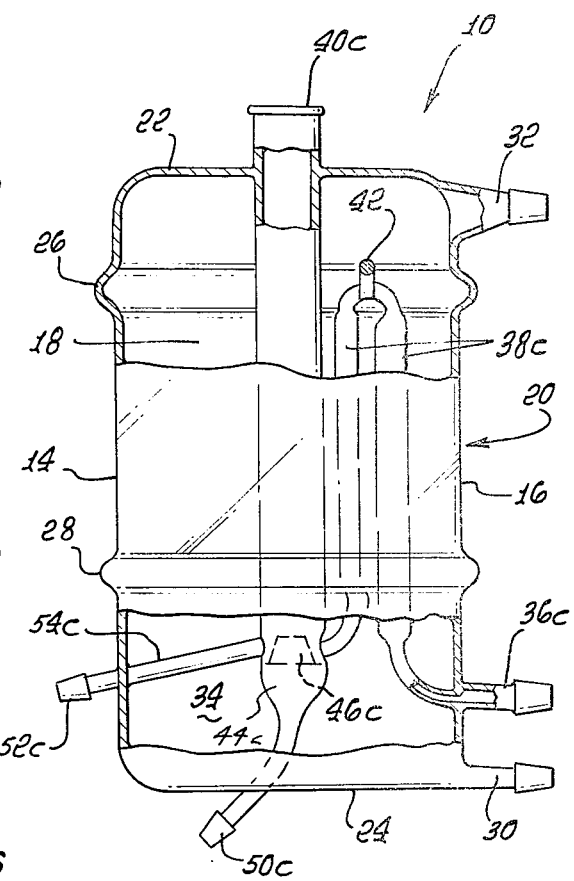
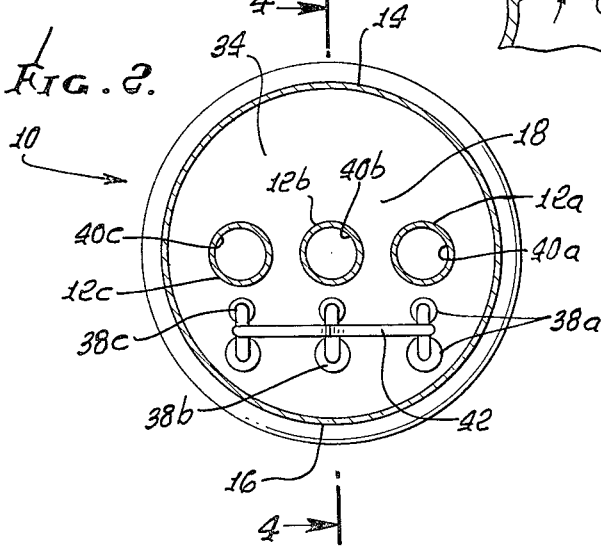
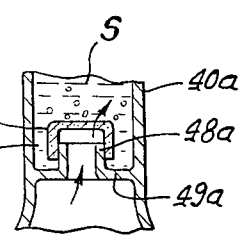
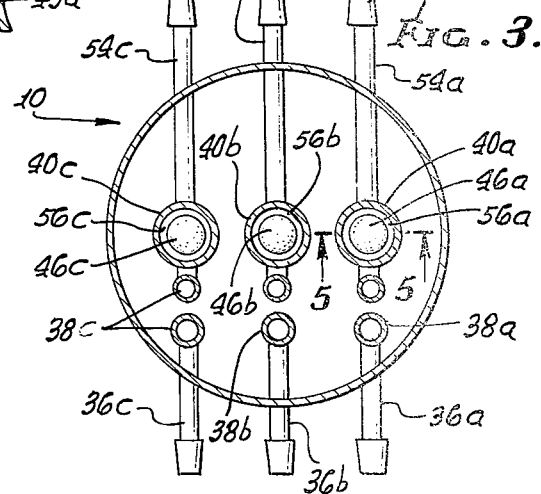

MULTIPLE INDEPENDENT PATH BUBBLE TONOMETER

BACKGROUND OF THE INVENTION

This invention has to do with bubble tonometers, and more particularly it is concerned with bubble tonometers having multiple independent flow paths which are maintained within a common environmentally controlled locus whereby sets of differing or identical blood samples may be simultaneously prepared under indentical though dynamic conditions.

Bubble tonometers have long been known; classically the bubble tonometer was designed as a closed system to prepared blood samples of different gas contents for the determination of oxygen disassociation curves. Bubble tonometers are simple devices which required no outside mechanism to agitate the blood and rapid equilibration is achieved. The history of bubble tonometers and a different type of bubble tonometer is discussed in an article entitled "Determination of the Blood/Gas Factor of the Oxygen Electrode Using a New Tonometer" by A. P. Adams and J. O. Morgan-Hughes published at Vol. 39, pp. 107–113 (1967) in the *British Journal of Anaesthesia*. Modern requirements for bubble tonometers are primarly fo maintaining blood/gas quality control. Thus in 1977 the Food and Drug Administration published a draft standard for blood/gas analysis establishing blood tonometery as a recommended procedure for blood/gas quality control. It was further recommended that such quality control should be maintained with three levels of tonometered blood at least once a week or every time an operating change is made, e.g. in membranes, electrodes, gas system shut-down and start-up. Daily performance is preferred. Use of the same gases to equilibrate the buffer is likewise recommended.

In general there is need to inexpensively and accurately produce blood and buffer controls at any desired oxygen level, either the low end, useful, for example, in connection with neonatal intensive care, or at the high end for supporting open heart surgery, or when conducting shunt studies.

It is highly undesirable to have simultaneous control of the various samples and buffer being prepared and it is to this need that the present invention is particularly directed.

SUMMARY OF THE INVENTION

It is accordingly an objective of the present invention to provide an improved tonometer. Other objectives include provision of a tonometer which is water thermostatic, multi-channeled, operates without electrical power, uses small amounts of gas, has the ability to produce tiny bubbles for fast evaluation, and is free of mechanical malfunction possibilities.

These and other objects of the present invention are achieved in accordance with the invention in a bubble tonometer apparatus adapted for preparing a predetermined gas/blood sample, which comprises in a controlled environment locus a gas/blood equilibration chamber, means to add a blood sample to the chamber, means to diffuse a gas into the blood sample to an equilibrium condition therein, the gas diffusion means including a porous diffuser body communicating the sample with a pressurized gas supply, and side arm means to selectively withdraw an aliquot portion of the equilibrium condition sample, the improvement comprisisng an elongated, cylindrical diffuser body extending freely into the chamber to define an annular space with the surrounding chamber wall for the diffusion of the gas radially into the blood sample for selective withdrawl of an aliqout portion thereof.

In particular embodiments the side arm means communicates with the chamber at the annular space; the diffusion means further includes reverse turn tubing for conducting gas to the diffuser body from beyond and through the controlled environment locus to the chamber; a closed vessel defining the environment locus; an annular flange within the chamber, the flange delimiting the chamber adjacently below the annular space and defining a seat for the diffuser body; the diffuser body being inverted cup-shaped and the seat comprising a tubular boss formed inwardly of the chamber flange in endwise diffuser seating relation.

In a highly preferred embodiment, the invention provides multiple, independent path bubble tonometer apparatus for preparing a plurality of predetermined like or different gas/blood samples under identical though dynamic conditions, which comprises in a controlled environment common locus multiple tonometer paths each of which is defined by a gas/blood equilibration chamber, means to add a blood sample to the chamber, means to diffuse a gas into the blood sample to an equilibrium condition therein, the gas diffusion means including a porous diffuser body communicating the sample with a pressurized gas supply, and side arm means to selectively withdraw an aliquot portion of the equilibrium condition sample; and an enclosure defining the controlled environment locus identically about each and every tonometer path for instantly cross-referenceable sample preparations.

As in previous embodiment, there is further contemplated each side arm means communicating with its respective chamber immediately adjacent its diffuser body, the diffuser body being elongated and interiorly void for radial diffusion of the gas into the blood and in such embodiments the side arm means may be radially opposite the diffuer body.

In a highly particularly preferred embodiment, there is provided triple independent path bubble tonometer apparatus for preparing three predetermined like or different gas/blood samples under identical though dynamic conditions, the apparatus comprising a closed glass housing defining an environmentally controlled locus and having an inlet and outlet for circulating controlled temperature water through the housing, and within the housing first second and third closed flow path tonometers each comprising an equilibrium chamber defined by a vertical tube opening upwardly to the top of the housing for blood sample reception and downwardly through the bottom of the housing for blood sample disposal, the chamber tube in its lower portion having an annular inward flange forming a tubular boss axially of the chamber, means to diffuse an equilibirum condition amount of a gas into the blood sample including reverse turn tubing leading from a pressurized gas supply beyond the housing and to the tubular boss, and a cup-shaped porous diffuser body mounted on the tubular boss in annular space defining and blood sample immersed relation, a side arm sampling port selectively communicating the blood sample within the annular space beyond the housing, and mounting means integrally formed on the housing for supporting the same in operating position.

BRIEF DESCRIPTION OF THE DRAWINGS

The invention will be further described as to an illustrative embodiment in conjunction with the attached drawings in which:

FIG. 1 is rear elevational view of the apparatus, partly broken away to show underlying parts;

FIG. 2 is a view in horizontal section taken on line 2—2 in FIG. 1;

FIG. 3 is a view in horizontal section taken on line 3—3 in FIG. 1;

FIG. 4 is a side elevational view of the apparatus, also partly broken away to show underlying parts; and FIG. 5 is a detail view greatly enlarged taken on line 5—5 in FIG. 3.

DESCRIPTION OF THE PREFERRED EMBODIMENTS

With reference now to the drawings in detail, a multiple path bubble tonometer is depicted at 10 having three independent flow paths 12a, 12b, 12c each with a common environmental locus 18 defined by the housing 20.

More particularly in FIGS. 1-4 blown glass housing 20 is of generally cylindrical shape having semi-cylindrical front and rear wall 14, 16 and closed at top and bottom with walls 22, 24 respectively. Housing 20 has integrally formed upper and lower annular ribs 26, 28 for securely mounting the tonometer 10 in operating position with conventional laboratory brackets (not shown). The housing 20 is provided at rear wall 16 with a water inlet 30 and outlet 32 through which temperature controlled water (not shown) is passed for thermostatic control of the housing interior 34. A series of gas inlets 36a, 36b, and 36c enter the housing through rear wall 16. Reverse turn tubing 38a, 38b and 38c communicates the gas inlets 36a-c with sample tubes 40a, 40b and 40c. Tubing 38a-c, supported in relative position by bridge 42, enters the sample tube 40a-c at the bottom side thereof just above collector bulbs e.g. 44c.

Within the tubes 40a-c are located the inverted cup-shaped porous diffusers 46a, 46b and 46c of the invention. Each diffuser, e.g. 46a, as best shown in FIG. 5 is mounted to a tubular boss 48a on flange 49a which continues the gas flow path beyond the tubing 38a. Noteworthy is the radial diffusion of the gas entering the diffuser 46a as the gas exerts like pressure through the space confined by the diffuser. This arrangement increases the rate of diffusion over a simple disk for a given gas pressure and also improves distribution into the blood sample S added through the top of and contained within the tube 40a (of FIG. 5).

Drain outlets, 50c for example, depend, downwardly from their respective tubes 40a-c and are normally provided with stop cocks not shown for convenience of illustration.

Sampling ports 52a, 52b and 52c are provided communicating through conduit 54a, 54b and 54c from beyond the housing front wall 14 into the tubes 40a-c. Standard fittings for sampling (not shown) are used to selectively close the ports 52a-c.

Importantly the conduits 54a-c enter into the tubes 40a-c adjacent the diffusers 46a-c to draw highly oxygenated samples from the annular spaces 56a, 56b and 56c immediately surrounding the diffuser.

In use then, the closed glass housing 20 is coupled to a water supply which passes from inlet 30 to outlet 32 providing a controlled temperature environment locus 18 within the housing. Blood sample S is introduced into the tubes 40a, 40b and 40c from the top, and gas from tubing 38a, 38b and 38c is introduced into the bottom. Upon achieving equilibrium in the spaces 56a, 56b and 56c samples may be withdrawn at ports 52 a-c. Used blood samples are drained through drain outlets 50a-c.

I claim:

1. In a bubble tonometer apparatus adapted for preparing a predetermined gas/blood sample, which comprises in a controlled environment locus a gas/blood equilibration chamber, means to add a blood sample to such chamber, means to diffuse a gas into said blood sample to an equilibrium condition therein, said gas diffusion means including a porous diffuser body communicating said sample with a pressurized gas supply, and side arm means to selectively withdraw an aliquot portion of the equilibrium condition sample, the improvement comprising an elongated circular cross-section diffuser body extending vertically within said chamber at least partly freely of the surrounding chamber wall to define a vertically extended annular space with said surrounding chamber wall for the diffusion of said gas radially into said blood sample for selective withdrawl of an aliquot portion thereof in highly oxygenated relation from said annular space immediately surrounding said diffuser body.

2. Bubble tonometer according to claim 1, in which said side arm means communicates with said chamber at said annular space.

3. Bubble tonometer according to claim 1, in which said diffusion means further includes reverse turn tubing for conducting gas to said diffuser body from beyond and through said controlled environment locus to said chamber.

4. Bubble tonometer according to claim 1, including also a closed vessel defining said controlled environment locus.

5. Bubble tonometer according to claim 1, including also an annular flange within said chamber, said flange delimiting said chamber adjacently below said annular space and defining a seat for said diffuser body.

6. Bubble tonometer according to claim 5, in which said diffuser body is inverted cup-shaped and said seat comprises a tubular boss formed inwardly of said chamber flange in endwise diffuser seating relation.

7. Multiple, independent path bubble tonometer apparatus for preparing a plurality of predetermined like or different gas/blood samples under identical though dynamic conditions, which comprises in a controlled enviroment common locus multiple tonometer paths each of which is define by a gas/blood equilibration chamber, means to add a blood sample to said chamber, means to diffuse a gas into said blood sample to an equilibrium condition therein, said gas diffusion means including a porous diffuser body communicating the sample with a pressurized gas supply, and side arm means to selectively withdraw an aliquot portion of the equilibrium condition sample; and an enclosure defining said controlled environment locus identically about each and every tonometer path for instantly cross-referenceable multiple sample preparations.

8. Apparatus according to claim 7, in which each said side arm means communicates with its respective chamber immediately adjacent its said diffuser body.

9. Apparatus according to claim 8, in which said diffuser body is elongated and interiorly void for radial diffusion of said gas into said blood.

10. Apparatus according to claim 9, in which said side arm means is radially opposite said diffuser body.

11. Triple independent path bubble tonometer apparatus for preparing three predetermined like or different gas/blood samples under identical though dynamic conditions, said apparatus comprising a closed glass housing defining an environmentally controlled locus and having an inlet and outlet for circulating controlled temperature water through the housing, and within said housing first, second and third closed flow path tonometers each comprising an equilibrium chamber defined by a vertical tube opening upwardly through the top of the housing for blood sample reception and downwardly through the bottom of the housing for blood sample disposal, said chamber tube in its lower portion having an annular inward flange forming a tubular boss axially of the chamber, means to diffuse an equilibrium condition amount of a gas into said blood sample including reverse turn tubing leading from a pressurized gas supply beyond said housing and to said tubular boss, and a cup-shaped porous gas diffuser body mounted on said tubular boss in annular space defining and blood sample immersed relation, a side arm sampling port selectively communicating the blood sample within said annular space beyond said housing, and mounting means integrally formed on said housing for supporting the same in operating position.

* * * * *